US009086405B2

(12) United States Patent
Connell et al.

(10) Patent No.: US 9,086,405 B2
(45) Date of Patent: Jul. 21, 2015

(54) ANIMAL STROKE MODEL

(75) Inventors: Barry James Connell, Charlottetown (CA); Tarek Saleh, Stratford (CA)

(73) Assignee: UNIVERSITY OF PRINCE EDWARD ISLAND, Prince Edward Island (CA)

( * ) Notice: Subject to any disclaimer, the term of this patent is extended or adjusted under 35 U.S.C. 154(b) by 239 days.

(21) Appl. No.: 13/579,487

(22) PCT Filed: Feb. 16, 2011

(86) PCT No.: PCT/CA2011/050097
§ 371 (c)(1),
(2), (4) Date: Aug. 16, 2012

(87) PCT Pub. No.: WO2011/100842
PCT Pub. Date: Aug. 25, 2011

(65) Prior Publication Data
US 2012/0322096 A1     Dec. 20, 2012

Related U.S. Application Data

(60) Provisional application No. 61/305,016, filed on Feb. 16, 2010.

(51) Int. Cl.
*A01K 67/027* (2006.01)
*G01N 21/78* (2006.01)
*G01N 33/50* (2006.01)

(52) U.S. Cl.
CPC .......... *G01N 33/5088* (2013.01); *A01K 67/027* (2013.01); *A01K 2207/30* (2013.01); *A01K 2267/0356* (2013.01)

(58) Field of Classification Search
IPC .................... A01K 67/027,2207/30, 2267/0356
See application file for complete search history.

(56) References Cited

PUBLICATIONS

Brain Ischemia from Wikipedia. Printout from http://en.wikipedia.org/wiki/Brain_ischemia pp. 1-7, printed Aug. 29, 2014.*
Bederson et al., "Rat Middle Cerebral Artery Occlusion: Evaluation of the Model and Development of a Neurologic Examination," Stroke. vol. 17, No. 3 pp. 472-476 (1986).
Broderick, J.P., and Hacke, W., "Treatment of Acute Ischemic Stroke. Part I: Recanalization Strategies," Circulation. vol. 106 pp. 1563-1569 (2002).
Buchan et al., "A New Model of Temporary Focal Neocortical Ischemia in the Rat," Stroke. vol. 23, No. 2, pp. 273-279 (1992).
Chen et al., "A Model of Focal Ischemic Stroke in the Rat: Reproducible Extensive Cortical Infarction," Stroke, vol. 17, No. 4 pp. 738-743 (1986).
Gerriets et al., "Complications and Pitfalls in Rat Stroke Models for Middle Ceebral Artery Occlusion: A Comparison Between the Suture and the Macrosphere Model Using Magnetic Resonance Angiography," Stroke. vol. 35 pp. 2372-2377 (2004).
Longa et al., "Reversible Middle Cerebral Artery Occlusion Without Craniectomy in Rats," Stroke. vol. 20 pp. 84-91 (1989).
Manabe et al., "Protection against focal ischemic injury to the brain by trans-sodium crocetinate: Laboratory investigation," Journal of Neurosurgery. vol. 113, No. 4 pp. 802-809 (2010).
Notification Concerning Transmital of International Preliminary Report on Patentability (Chapter I of the Patent Cooperation Treaty) corresponding to International Patent Application No. PCT/CA2011/050097 dated Aug. 30, 2012.
Notification of Transmittal of the International Search Report and the Written Opinion of the International Searching Authority, or the Declaration corresponding to International Patent Application No. PCT/CA2011/050097 dated Apr. 28, 2011.
Reddy, M.K., and Labhasetwar, V., "Nanoparticle-mediated delivery of superoxide dismutase to the brain: and effective strategy to reduce ischemia-reperfusion injury," The FASEB Journal. vol. 23 pp. 1384-1395 (2009).
Saleh et al., Am. J. Physiol. Regulatory Integrative Comp. Physiol. vol. 281 pp. 1531-1539 (2001).
Slivka et al., "Table 2," Stroke. vol. 26 pp. 1061-1066 (1 page) (1995).
Tamura et al., "Focal Cerebral Ischaemia in the Rat: 1. Description of Technique and Early Neuropathological Consequences Following Middle Cerebral Artery Occlusion," Journal of Cerebral Blood Flow and Metabolism. vol. 1, No. 1 pp. 53-60 (1981).

* cited by examiner

*Primary Examiner* — Marcia S Noble
(74) *Attorney, Agent, or Firm* — Jenkins, Wilson, Taylor & Hunt, P.A.

(57) ABSTRACT

An animal stroke model is provided. The model is useful in the study of brain ischemia and/or reperfusion injury and in identification and testing of compounds and interventions useful in the treatment of stroke. The method is carried out in a non-human mammal, such as rat. The method of inducing ischemia and/or reperfusion injury involves exposing a portion of the middle cerebral artery (MCA) and temporarily occluding it at one or more distinct locations, preferably three distinct locations. The model results in highly reproducible and focal infarct sizes, with low rate of mortality during the experimental procedure.

20 Claims, 7 Drawing Sheets

Figure 9 time (minutes) after occlusion of guanosine administration

ANIMAL STROKE MODEL

CROSS REFERENCE TO RELATED APPLICATIONS

This application claims the benefit of priority to PCT International Patent Application Ser. No. PCT/CA2011/020097, filed Feb. 16, 2011, which itself claims the benefit of priority to Provisional Application Ser. No. 61/305,016, filed Feb. 16, 2010, each of which is incorporated herein by reference in its entirety.

FIELD OF THE INVENTION

The present invention relates generally to an animal model of stroke. More particularly, the invention relates to a method of inducing reproducible brain ischemia and/or reperfusion injury in a non-human mammal, and uses thereof.

BACKGROUND OF THE INVENTION

A stroke is the rapidly developing loss of brain function(s) due to disturbance in the blood supply to the brain. This can occur due to a hemorrhage or due to ischemia (lack of oxygen and/or glucose supply) which may be caused, for example, by thrombosis or embolism. During ischemic stroke, blood flow to an area of the brain is blocked and, consequently, that area of the brain begins to cease function and will ultimately die. The initial area of neuronal death is called the ischemic core. Over time, irreversible injury will occur, often leading to death of the tissue, i.e. "infarction". In the area of acute stroke research, considerable focus has been directed toward unraveling the mechanisms contributing to cellular necrosis resulting from prolonged ischemia in regions of the brain.

The return of blood flow to the ischemic area, known as "reperfusion", may occur either spontaneously or as a result of a clot busting drug. Reperfusion is essential for the recovery of the brain area surrounding the ischemic core. However, in a detrimental and paradoxical response, the return of blood flow can increase cerebral edema and cause further brain damage, for example, through the introduction of free radicals (Dietrich, W. D. (1994) Morphological manifestations of reperfusion injury in brain. *Ann NY Acad Sci,* 723: 15-24); Aronowski, J. et al. (1997) Reperfusion injury: demonstration of brain damage produced by reperfusion after transient focal ischemia in rats. *J Cereb Blood Flow Met,* 10: 1048-1056). This further damage is known as "reperfusion injury".

Tissue-plasminogen-activator (tPA), a clot-busting drug, is the only clinically effective neuroprotectant currently administered following a stroke. However, tPA therapy is limited to administration within four hours of the onset of clinical signs of stroke, due to the detrimental effects of reperfusion injury (Kuroda, S. and B. K. Siesjo (1997) Reperfusion damage following focal ischemia pathophysiology and therapeutic windows. *Clin Neurosci,* 4: 199-212). It has been found that, after 4 hours, the damage due to reperfusion injury can exceed the damage caused by the prolonged ischemia.

Many pathological responses are involved in cerebral reperfusion injury, including but not limited to the introduction of superoxides, free radicals and leukocytes, platelet activation, and breakdown of the blood-brain barrier (Kamat C. et al. (2008). Antioxidants in central nervous system diseases: Preclinical promise and translational challenges. *J Alzheimers Dis,* 15: 473-493; Martin, R. L. (1997) Experimental neuronal protection in cerebral ischaemia Part 1: Experimental models and pathophysiological responses. *J Clin Neuroscience,* 4: 96-113).

Strategies to reduce or minimize cerebral reperfusion injury require an understanding of the various pathophysiological processes involved.

Various animal models have been developed in an attempt to study the effects of ischemia and/or reperfusion in various tissues, including animal models of ischemic stroke. The available models of ischemic stroke have limitations. One significant limitation of prior art models is high mortality rate during the experimental procedure. Another significant limitation of prior art models is a lack of reproducibility, and thus high variability, with respect to infarct size and/or location. A reproducible and focal ischemia is ideal. Thus, there is a long-felt need in the art for improved animal models having lower mortality rates and higher reproducibility (lower variability) compared to prior models.

Several prior animal models of ischemic stroke have examined the effects of permanent occlusion of the middle cerebral artery (MCA), one of three major paired arteries that supply blood to the cerebrum. For example, Robinson and colleagues studied permanent ligation of the MCA in rats (Robinson, R. G., et al. (1975) *Nature,* 255(5506): 332-334). Bederson and colleagues produced extensive (3 or 6 mm) occlusions of the MCA in rats by exposing the MCA transcranially and irreversibly occluding it with microbipolar coagulation (Bederson, J. B. et al. (1986) *Stroke,* 17: 472-476), and Tamura and colleagues used electrocautery to permanently occlude the MCA (Tamura, A., et al. (1981) *Journal of Cerebral Blood Flow and Metabolism,* 1(1): 53-60). Saleh and colleagues describe a method of permanently occluding the MCA at three locations using electrocautory (Saleh et al. (2001) *Am J Physiol Regulatory Integrative Comp Physiol* 281:2088-2095; Saleh et al. (2001) *Am J Physiol Regulatory Integrative Comp Physiol* 281:1531-1539) to study the immediate effects of permanent MCA occlusion (within 4-6 hours of occlusion). The three-point approach resulted in focal infarct areas restricted to the cerebral cortex with an associated intraoperative mortality rate of less than 1%. Chen et al. disclose a method of surgically exposing the right MCA in rats and permanently occluding it with a square knot using a suture, with or without simultaneous ligation of the right common carotid artery (CCA) or left and right CCA together (Chen, S. T. et al. (1986) *Stroke,* 17: 738-743). In one method, the MCA and right CCA were permanently occluded, while the left CCA was temporarily compressed by a clip. Using the latter method, mortality was lowered to 7% and infarcts were observed at a rate of 96%. However, infarct volume was quite large (100±6 mm).

While permanent occlusion of the MCA can provide a means of studying ischemic events involved in a stroke, such models do not permit examination of the effects of subsequent reperfusion.

Longa and colleagues described an animal model of ischemic stroke involving reversible occlusion of the MCA in rats (Longa, E. Z. et al. (1989). *Stroke,* 20: 84-91). The method involved introducing a silk suture through an incision in a terminal branch of the external carotid artery (ECA) and advancing the suture into the internal carotid artery (ICA) lumen until resistance was met, indicating that the end of the suture had passed the MCA origin and reached the proximal segment of the anterior cerebral artery (ACA), which has a smaller diameter. The incision was closed, leaving 1 cm of the suture protruding. This permitted manual withdrawal of the suture to permit reperfusion through restoration of MCA blood flow. However, due to variations in anatomy (for instance, differences in the MCA of each animal), it is difficult to place the end of the string in the same place in each animal. It is impossible to visualize and confirm the site of occlusion, the occurrence and extent of occlusion, and the extent of reperfusion. As such, the reversibly occluded animal model of Longa et al. (and other animal models based thereupon) is highly variable in terms of suture placement, occurrence of infarction, infarct size (21.9±14.5% and 25.7±13.4% for 2- and 4-hour occlusions, respectively) and neurological score of the resulting animals.

Reddy and colleagues disclosed an improvement on the method of Longa et al. (supra) which involved coating the suture with poly-L-lysine to promote adhesion of the suture end to the blood vessel endothelial lining (Reddy, M. K. and V. Labhasetwar (2009). *FASEB Journal*, 23: 1384-1395). However, this method suffers from many of the same disadvantages of the Longa et al. method in that the placement of the suture and extent of occlusion and reperfusion cannot be visually confirmed or assessed. The infarct volume was also relatively large (48.7±3.7 mm in control animals). Advancement of a monofilament (suture) through a vessel, as described by Longa et al. and Reddy et al. can damage the endothelium (see below).

Buchan and colleagues described a method of temporarily occluding the MCA using a microclip in male Wistar rats and spontaneously hypertensive rats (SHRs) (Buchan, A. M. et al. (1992). *Stroke*, 23: 273-279). In this method, the right and left common carotid arteries (CCA) were permanently or temporarily occluded through ligation, while the right MCA was surgically exposed and temporarily occluded using a microclip. Reperfusion was initiated by removing the microclip after 1 to 4 hours. This method permitted direct visual verification of MCA occlusion and reperfusion. Simultaneous occlusion of the right and left CCA and the right MCA resulted in lower variability in infarct size in SHRs. However, there was greater variability in infarct size in the healthy Wistar rats (see Buchan et al. at page 277, paragraph 1) and studies of SHR rats may not be representative. Slivka and colleagues reported permanent occlusion of the right CCA with temporary, microclip-induced occlusion of the right MCA. However, this yielded a variable infarct size in male SHRs. (Slivka, A. et al. (1995). *Stroke*, 26: 1061-1066; see Table 2).

Microclips are expensive and are known to damage the vascular endothelium. In some cases, adhesion of the clipped vessel occurs which results in incomplete and/or inconsistent reperfusion. Damaged endothelium (using clips or a monofilament advanced through CCA) can lead to release of endothelial factors which can increase brain damage or trauma on their own. Therefore, using such methods, it can be difficult to assess stroke damage induced by occlusion and/or reperfusion versus damage due to release of endothelial factors.

Manabe and colleagues reported a method of inducing temporary focal ischemia by temporarily occluding the right and left CCAs and the MCA (Manabe et al. (2009). *Journal of Neurosurgery*, electronically published Dec. 4, 2009). In this method, each CCA was exposed and a polypropylene suture was passed around a CCA and through a polyethylene tube to form a loose snare around each CCA. The MCA was exposed and temporary, three-vessel occlusion was induced by clipping the MCA with a microclip (at a point distal to the origin of the lenticulostriate arteries) and simultaneously closing the suture loops around the CCAs. The occlusion was maintained for 2 hours or 24 hours. However, the clinical relevance of the animal stroke model of Manabe et al. is questionable, as human stroke patients do not experienced occlusions of both carotids (leading to a global decrease in blood flow) in addition to occlusion of a vessel, such as the MCA.

One major hinderance of stroke research is the lack of good animal models. Questionable clinical relevance, surgery-induced damage, and/or mortality during the experimental procedure are problems in existing animal models (Gerriets T. et al. (2004). Complications and pitfalls in rat stroke models for middle cerebral artery occlusion: A comparison between the suture and the macrosphere model using magnetic resonance angiography. *Stroke*, 35: 2372-2377; Martin 1997). A high level of mortality during the procedure brings into question both the validity of the model and the ability of the data gleaned from the surviving animals to be representative of the group (Broderick and Hacke (2002). Treatment of acute ischemic stroke: Part 1: recanlization strategies. *Circulation*, 106: 1563-9). Lack of reproducibility in the size and location of the infarct produced is another problem. There remains a need for improved animal models of ischemic stroke and reperfusion injury that are more clinically relevant with highly reproducible focal infarctions, low incidence of artery damage, and low mortality rate during the experimental procedure.

SUMMARY OF THE INVENTION

It is an object to obviate or mitigate at least one disadvantage of previous animal models of brain ischemia and/or reperfusion.

In one aspect, there is provided a method of inducing reproducible ischemia and/or reperfusion injury in a non-human mammal.

In one aspect, there is provided a method of inducing reproducible brain ischemia and/or reperfusion injury in a non-human mammal, comprising the steps of: exposing a portion of the middle cerebral artery (MCA) in the non-human mammal, temporarily occluding said MCA at a first location, a second location, and a third location to substantially occlude blood flow; maintaining said occlusion for a desired occlusion time; and optionally, releasing said occlusion to restore blood flow and maintaining said restored blood flow for a desired reperfusion time.

In one embodiment, the first location is proximally dorsal to the rhinal fissure, the second location is proximally ventral to bifurcation of said MCA to the frontal and parietal cortices, and, the third location is proximal to bifurcation of said MCA along the parietal cortex.

In one embodiment, a suture material is used to temporarily occlude said MCA at said first, second and third locations.

In one embodiment, to provide the temporary occlusion, a first suture is threaded behind said MCA at said first location, a second suture is threaded behind said MCA at said second location, and a third suture is threaded behind said MCA at said third location.

In one embodiment, a suitable force is applied to the first suture in a direction substantially perpendicular to the axis of the MCA at the first location to occlude said MCA at said first location, and wherein placement of the second and third sutures behind the MCA at the second and third locations is sufficient for occlusion at said second and third locations.

In one embodiment, said first suture comprises 000-braid silk, said second suture comprises Prolene™ blue monofilament size 3-0, and said third suture comprises Prolene™ blue monofilament size 4-0.

In some embodiments, the occlusion time is about 0.1 to about 10 hours, or about 0.5 to about 6 hours, or about 0.5 to about 1 hour.

In some embodiments, the reperfusion time is about 0.1 to about 10 hours, or about 3 to about 10 hours, or about 4 to about 6 hours.

In one embodiment, the occlusion time is about 0.1 hour to about 1 hour and the reperfusion time is about 4 to about 6 hours. In another embodiment, the occlusion time is about 0.5 hours and the reperfusion time is about 5.5 hours.

In another aspect, there is provided a method of identifying a compound or intervention useful in the treatment, reduction or prevention of ischemia and/or reperfusion injury comprising the steps of: carrying out an embodiment of a method disclosed herein on a test animal which is a non-human mammal; administering a test compound or intervention to the test animal prior to, during and/or after administering the method; and assessing the extent of injury compared to an appropriate control animal, wherein decreased injury in the test animal compared to the control animal is indicative that the compound or intervention is useful in the treatment, reduction or prevention of ischemia and/or reperfusion injury.

In some embodiments, the non-human mammal is a rodent. In some embodiments, the rodent is a rat.

In another aspect, there is provided a method of inducing reproducible brain ischemia and/or reperfusion injury in a rat, comprising the steps of: exposing a portion of the middle cerebral artery (MCA) in the rat; temporarily occluding said MCA at a first location, a second location, and a third location to substantially occlude blood flow, wherein the first location is proximally dorsal to the rhinal fissure, the second location is proximally ventral to bifurcation of said MCA to the frontal and parietal cortices, and, the third location is proximal to bifurcation of said MCA along the parietal cortex; maintaining said occlusion for an occlusion time of about 0.1 hour to about 1 hour; releasing said occlusion to restore blood flow; maintaining said restored blood flow for a reperfusion time about 4 to about 6 hours; and assessing the type and extent of injury produced.

In another aspect, there is provided a method of identifying a compound or intervention useful in the treatment, reduction or prevention of ischemia and/or reperfusion injury comprising the steps of: exposing a portion of the middle cerebral artery (MCA) in a test animal which is a rat; temporarily occluding said MCA at a first location, a second location, and a third location to substantially occlude blood flow, wherein the first location is proximally dorsal to the rhinal fissure, the second location is proximally ventral to bifurcation of said MCA to the frontal and parietal cortices, and, the third location is proximal to bifurcation of said MCA along the parietal cortex; maintaining said occlusion for an occlusion time of about 0.1 hour to about 1 hour; releasing said occlusion to restore blood flow; maintaining said restored blood flow for a reperfusion time about 4 to about 6 hours; administering a test compound or intervention to the test animal prior to, during and/or after the occlusion period and/or the reperfusion period; and assessing the extent of injury compared to an appropriate control animal, wherein decreased injury in the test animal compared to the control animal is indicative that the compound or intervention is useful in the treatment, reduction or prevention of ischemia and/or reperfusion injury.

In one embodiment, the occlusion time is about 0.5 hours and the reperfusion time is about 5.5 hours.

In another aspect, there is provided a use of a method disclosed herein to identify a compound and/or intervention useful in the treatment, reduction or prevention of ischemia and/or reperfusion injury.

In another aspect, there is provided an animal model of ischemic stroke and/or reperfusion injury comprising carrying out a method as disclosed herein.

Other aspects and features will become apparent to those ordinarily skilled in the art upon review of the following description of specific embodiments of the invention in conjunction with the accompanying figures.

BRIEF DESCRIPTION OF THE DRAWINGS

Embodiments of the present invention will now be described, by way of example only, with reference to the attached Figures, wherein.

DETAILED DESCRIPTION

The present invention relates generally to an animal model for the study of stroke. More particularly, the invention relates to a method of inducing reproducible brain ischemia and/or reperfusion injury in a non-human mammal, and uses therefor.

The method involves exposing, e.g. surgically, the middle cerebral artery (MCA) and temporarily occluding the MCA at one or more locations.

In one embodiment, the method involves temporarily occluding the MCA at three locations to produce an animal model of brain ischemia and/or reperfusion injury that is highly reproducible, yielding small focal infarcts that are primarily localized to the cerebral cortex, with low mortality rate during the surgical procedure.

Figure 1:
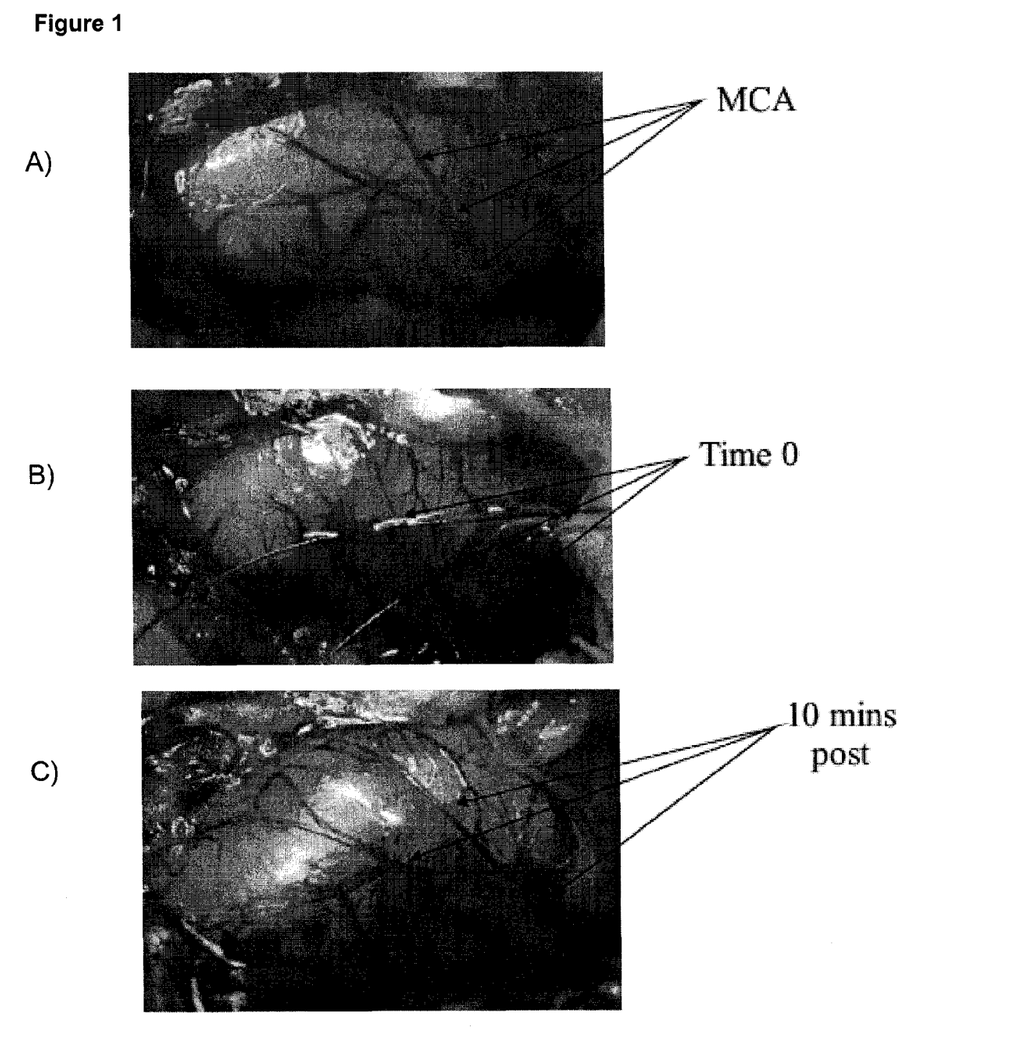
FIG. 1 illustrates placement of sutures to temporarily occlude the middle cerebral artery at three locations in accordance with an embodiment of the invention.
Figure 3:
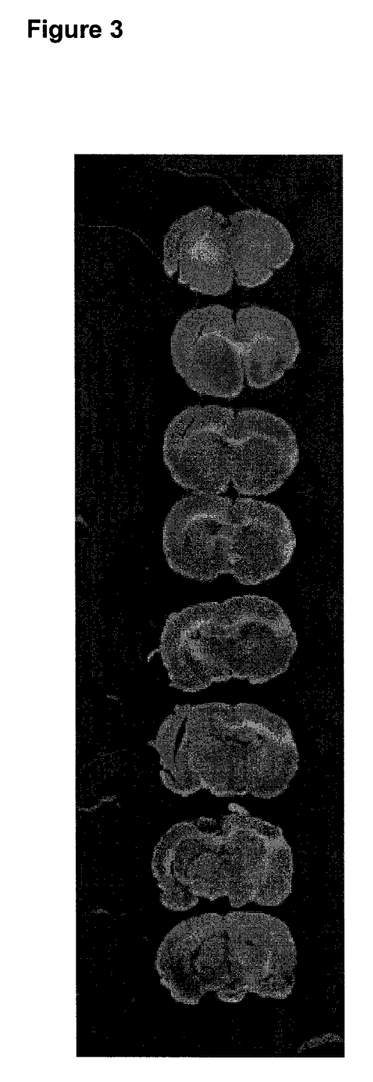
FIG. 3 depicts serial sections of a brain following 30 minutes of occlusion followed by 5.5 hours of reperfusion, according to one embodiment of the invention.

In some embodiments, the method of inducing temporary middle cerebral artery occlusion (MCAO) is carried out by occluding the MCA at 3 points on selected branches of the MCA (see FIG. 1 for precise locations). With this information, A skilled person will recognize that the occlusions can be made in any suitable location along these branches to produce a reproducible focal stroke, as illustrated in FIG. 3.

In one embodiment, the method comprises the steps of: exposing a portion of the MCA in a non-human mammal, such as a rodent; temporarily occluding said MCA at a first location, a second location, and a third location to substantially block blood flow; maintaining said occlusion for a desired occlusion time; releasing said occlusion to restore blood flow; and optionally, maintaining said restored blood flow for a desired reperfusion time.

In some embodiments, the first location is proximally dorsal to the rhinal fissure, the second location is proximally ventral to bifurcation of said MCA to the frontal and parietal cortices, and, the third location is proximal to bifurcation of said MCA along the parietal cortex.

The temporary occlusion may be provided using any means suitable for applying enough pressure to the vessel to substantially occlude bloodflow. By substantially, it is meant that at least about 80%, or more typically at least about 85%, 90%, 95%, 99% or 100%, bloodflow is occluded. Laser Doppler flow recorded in the region of the MCA (see Connell and Saleh, Neurosci Methods, 190:28-33, 2010) has been used to confirm that, in accordance with embodiments disclosed herein, blood flow can be totally occluded (100%), and flow returns to ~110% following release of the occlusion. This "over-reperfusion" compared to pre-occlusion blood flow values is similar to the phenomenon observed clinically in patients, further validating the present animal model.

In some embodiments, a suture material or microclip is used to occlude the vessel. Preferably, the selected means does significantly damage the vessels. In some embodiments, a suture material is used. Suture material thickness and tension may be adjusted to apply pressure sufficient to occlude vessels of different size. When a suture material is used, it may optionally be coated in wax or other friction-reducing coating.

In some embodiments, the non-human mammal is a rodent, such as a rat, mouse, hamster or guinea pig. In some embodiments, the non-human mammal is a rat. Various strains of rat are commonly used in research and will be known to the skilled person.

In some embodiments, the method of inducing temporary middle cerebral artery occlusion (MCAO) may be carried out in accordance with the method described further below in Example 1. Animals may be placed in a stereotaxic frame, such as a David Kopf (Tujunga, Calif, USA), and the right MCA may be approached through a rostra-caudal incision of the skin and frontalis muscle at the approximate level of bregma. The frontalis and temporalis muscles may be reflected anteriorly and posteriorly to expose the squamosal bone to the point where the zygoma and the squamosal bone fuse. A portion of the squamosal bone may be removed to expose the middle cerebral artery. In some embodiments, the bent tip of a 25-gauge hypodermic needle may be used to cut and retract the dura mater above the MCA. Blood flow through the MCA may be impeded by the placement of surgical suture behind the MCA at 3 designated positions along the exposed vessel. The first suture (which may be, in some embodiments, 000-braided silk; Ethicon, N.J., USA) placement may be just dorsal to the rhinal fissure. A 20 cm length of suture may be used, in some embodiments. Half the length of the suture may be threaded behind the MCA. The two ends may then be gently pulled together and, in some embodiments, taped to the ear bars so that the resulting pressure on the MCA is sufficient to impede blood flow. The second suture (which may comprise, in some embodiments, 3-0 PROLINE™ brand blue monofilament, which may be about 2 cm in length; Ethicon, N.J., USA) may be threaded behind the MCA just proximal to the bifurcation of the MCA of the MCA to the frontal and cortices, and the third suture (which may be, in some embodiments, 4-0 PROLINE™ brand monofilament, which may be 2cm in length; Ethicon, N.J., parietal cortex. The ends of the second and third suture may be placed so that the middle of the sutures applies pressure to the MCA from behind and impedes blood flow through the MCA. It is important to note that, in accordance with this method, the vessels are not tied off with the suture material. The pressure applied by the suture material is sufficient to occlude the vessel without the need for forceably restricting the vessel with ties or clips, which can result in permanent occlusion and/or damage the vessels. A skilled reader would readily appreciate that certain modifications of this method would be possible.

In some embodiments, the temporary occlusion may be maintained for 0.1 to 10 hours. This may be referred to as the occlusion time. In some embodiments, the occlusion time is about 0.1, 0.2, 0.3, 0.4, 0.5, 1, 2, 2.5, 3, 3.4, 4, 4.5, 5, 5.5 or 6, 7, 8, 9, or 10 hours. In one embodiment, the occlusion time is about 0.5 to about 6 hours. In another embodiment, the occlusion time is about 0.5 to about 2 hours. In another embodiment, the occlusion time is about 0.5 to about 1 hour. In another embodiment, the occlusion time is about 0.5 hours.

Where a study of reperfusion is desired, blood flow through the MCA (reperfusion) may be restored by release of the occlusion pressure on the vessels. For instance, by release of the suture ends where the suture is pulled to applied force and/or removal of the sutures from behind the vessel, or removal of the clips if clips are used. In some embodiments, reperfusion may be allowed to occur for a reperfusion time of 0.1 to 10 hours. For instance, in some embodiments, reperfusion may occur for about 0.1, 0.2, 0.3, 0.4, 0.5, 1, 2, 2.5, 3, 3.4, 4, 4.5, 5, 5.5 or 6, 7, 8, 9, or 10 hours. In one embodiment, the reperfusion time is about 3 to 10 hours. In another embodiment, the reperfusion time is about 4 to 6 hours. In another embodiment, the reperfusion time is about 5.5 hours.

Any occlusion time mentioned above may be combined with any reperfusion time mentioned above in order to carry out embodiments of the disclosed method. A skilled person can determine the optimal occlusion and/or reperfusion time for a given animal.

In one embodiment, the occlusion time is about 0.5 to 2 hours and the reperfusion time is about 3 to 10 hours, before animals are further studied. In another embodiment, the occlusion time is about 0.5 hours (30 minutes) to 1 hour and the reperfusion time is about 4 to 6 hours. In another embodiment, the occlusion time is about 0.5 hours and the reperfusion time is about 5.5 hours. In another embodiment, the occlusion time is about 2 hours and the reperfusion time is about 4 hours. In another embodiment, the occlusion time is about 0.5 hours and the reperfusion time is about 5.5 hours.

In accordance with embodiments disclosed herein, the method results in a highly focal infarct volume substantially restricted to the cerebral cortex, with minimal surgery-induced mortality. In some embodiments, the infarct size is less than 30 mm$^3$. In some embodiments, the infarct size is less than 20 mm$^3$. In some embodiments, it is less than 10 mm$^3$.

The time course study (see Example 2), using methods according to some embodiments, revealed that leaving the sutures in place for 4 to 6 hours may produce the greatest infarct volumes.

Figure 4:
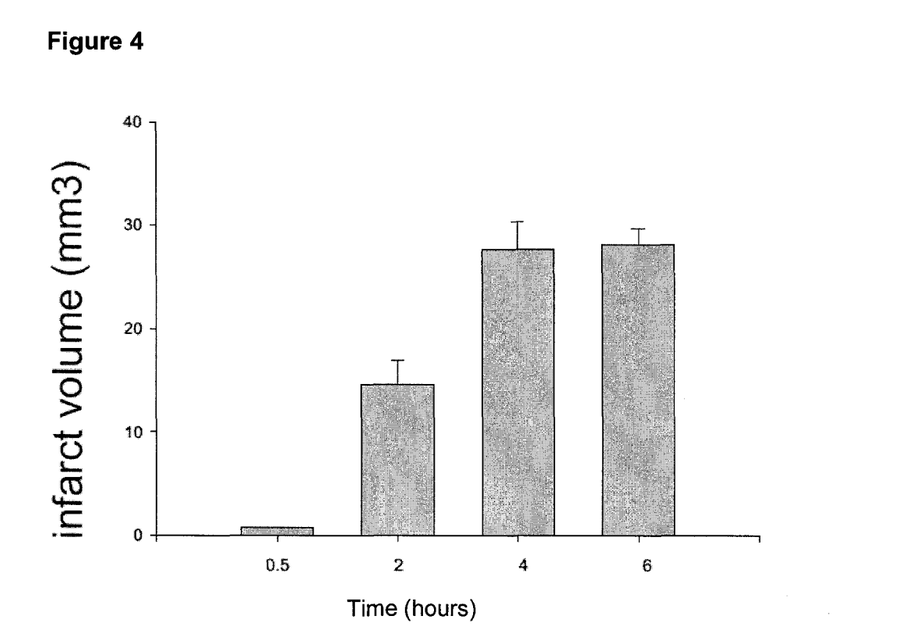
FIG. 4 is a graph depicting infarct volume versus time of occlusion in methods according to certain embodiments of the invention.
Figure 5:
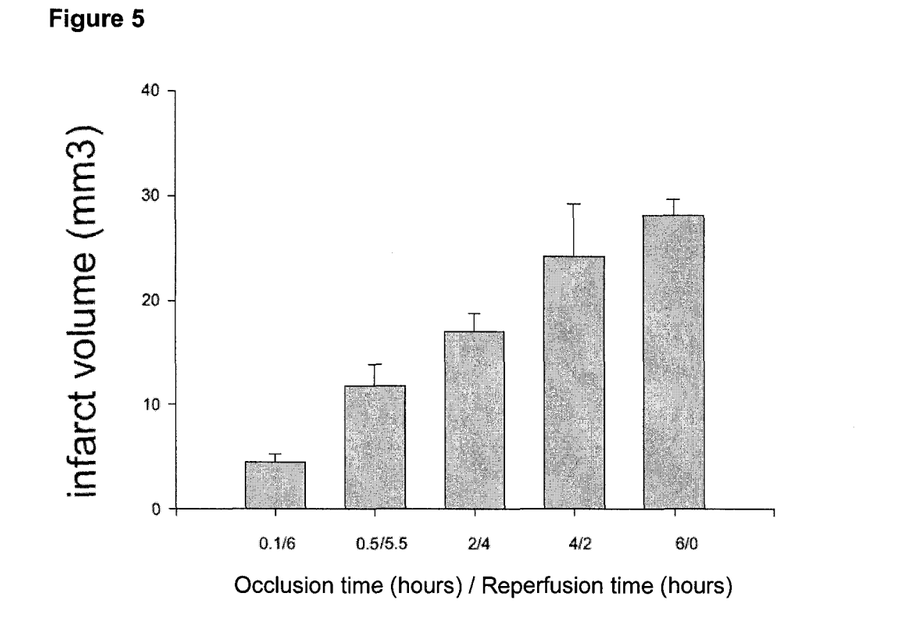
FIG. 5 is a graph depicting infarct volume for methods involving combinations of occlusion time and reperfusion time according to certain embodiments of the invention.

In Example 3, a 30-minute occlusion followed by 5.5 hours of reperfusion produced a significantly greater infarct volume when compared to the infarct volume produced by the occlusion alone (e.g. compare FIG. 4, 0.5-hour data point to FIG. 5, 0.5-hour occlusion+5.5-hour reperfusion (0.5/5.5) data point). The larger infarct volume may be due to reperfusion injury. Therefore, this combination, may be particularly useful in studying reperfusion injury, including underlying mechanisms, and treatment and prevention thereof. A skilled person would readily appreciate that variations in these times may be encompassed in some embodiments.

The reversible occlusion and reperfusion method, according to certain embodiments, provides a low rate of mortality of less than about 5 percent. In other embodiments, mortality rate is less than 4%. In other embodiments, it is less than 3%. In further embodiments, the mortality rate is about 2%. Thus, the data which results from studies using the methods described herein may be considered as being more representative of a drug-induced effect in reducing infarct volume (i.e. neuroprotection) as opposed to an effect that is only observed only in animals strong enough to survive surgery. As such, the methods described herein provide a useful and relevant animal model of human stroke.

Following the experimental procedure, animals may be sacrificed or further studied. The skilled person will be able to determine appropriate investigations and assays to be performed depending on what is being researched. In some cases, the purpose of the research may be to study the process of ischemia an/or reperfusion injury. In other cases, the purpose may be to study or identify compounds or interventions useful in the treatment, reduction or prevention of injury associated with ischemia and/or reperfusion. In some cases, the purpose may be to study or identify compounds or interventions useful in the treatment, reduction or prevention of injury associated with stroke.

To validate the present methods as an animal model of stroke which permits examination of ischemia and, optionally, reperfusion events, drugs which were previously shown to be neuroprotective in humans and other animal stroke models were tested in the present animal model according to embodiments disclosed herein. Specifically, estrogen, edaravone and guanosine were tested. The beneficial effects of estrogen administration have been previously demonstrated and edaravone was chosen because it has been shown to be protective in many different models of reperfusion injury due to its powerful free radical scavenger effects. Guanosine is also a known neuroprotectant.

Figure 6:
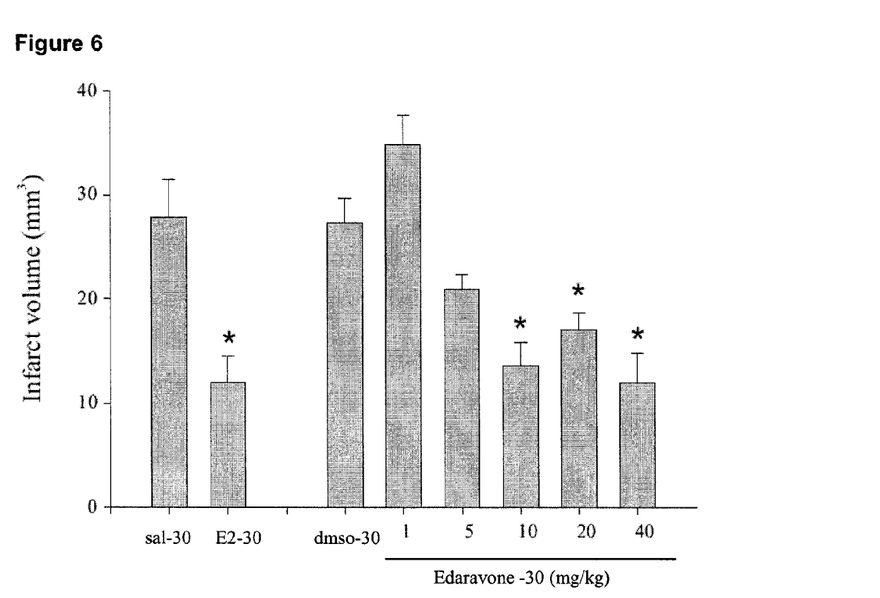
FIG. 6 is a graph depicting the effect of endarvone on infarct volume due ischemia induced for various times using methods according to certain embodiments of the invention.

The administration of estrogen (E2) or edaravone provided significant levels of neuroprotection when either drug was given 30 minutes prior to the onset of a 6-hour occlusion of the MCA (see Example 4 and FIG. 6). The observed neuroprotective effect of edaravone suggests that at least part of the growth of the infarct area during reperfusion may be due to the presence of free radicals, since the main effect of edaravone is the ability to act as a free radical scavenger.

Figure 7:
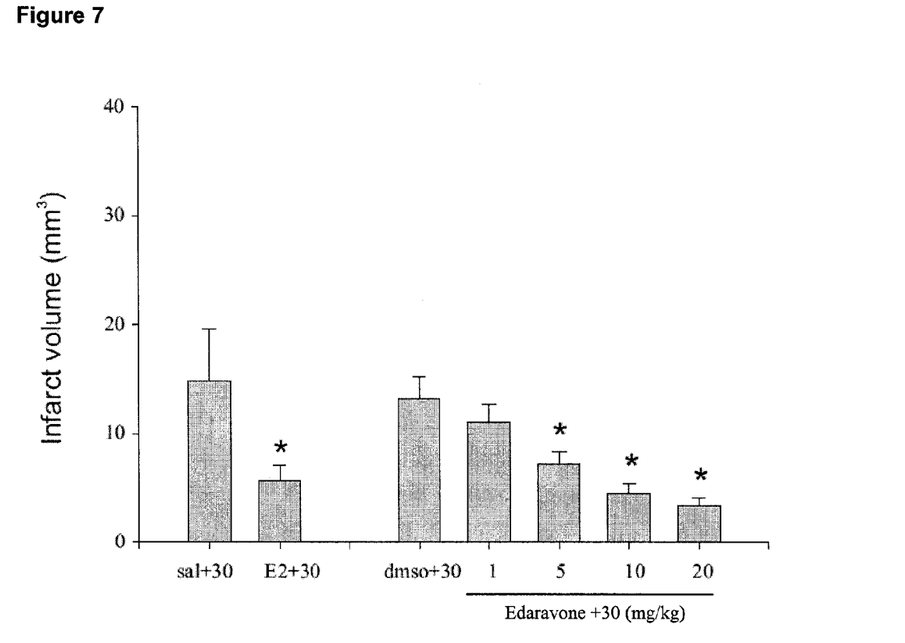
FIG. 7 is a graph depicting the effect of endarvone on infarct volume due ischemia and reperfusion injury induced for various times using methods according to certain embodiments of the invention is according to certain embodiments of the invention.

Estrogen and edaravone also showed neuroprotective abilities when administered just before removal of the sutures after 30 minutes of MCAO (see Example 4 and 'E2+30' and Edaravone+30' data points in FIG. 7). The administering of these drugs after removal of sutures permitted study of the potential beneficial effects of these drugs on reperfusion-induced injury alone since the infarct core due to the initial stoppage of blood flow would have already developed by the time of administration. Part of the neuroprotective effects of estrogen has been previously described as its ability to act as an antioxidant and a free radical scavenger. These results further support the idea that estrogen may produce at least some of its neuroprotection via free radical scavenging, since the production of free radicals has been demonstrated by many labs to result following the beginning of reperfusion. Edaravone also produced very powerful neuroprotection when administered just prior to removal of the sutures. This result was expected and confirms that the growth in infarct size following the removal of sutures was due to the presence of free radicals. A free radical scavenger, such as edaravone, would be expected to provide relief to deleterious effects of the presence of free radicals.

Figure 8:
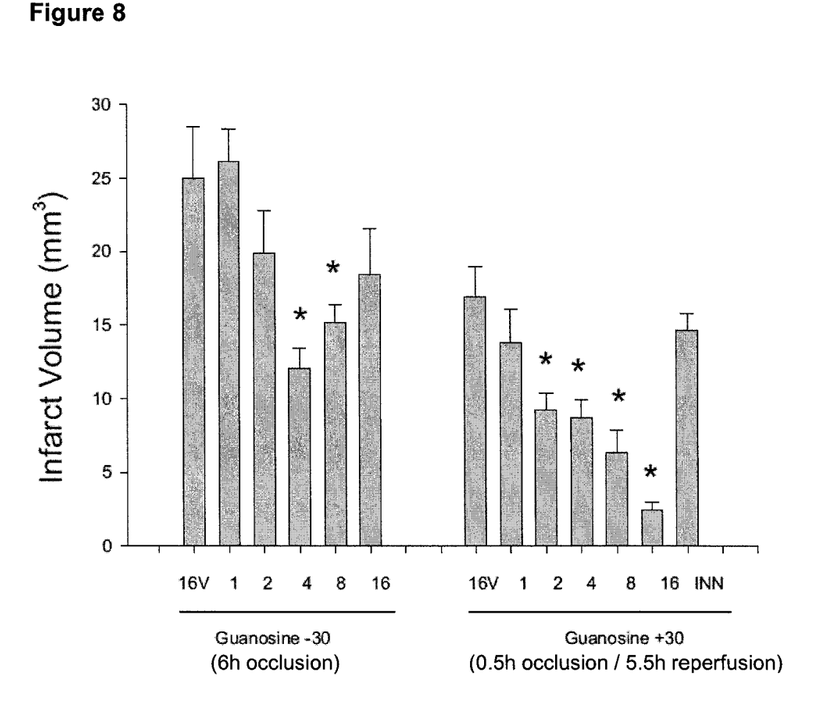
FIG. 8 is a graph depicting the effect of guanosine injected before and after occlusion on infarct volume following ischemia and/or reperfusion induced using methods according to certain embodiments of the invention.

Injection of guanosine 30 minutes before 6 hours of occlusion ("permanent" occlusion) reduced infarct size (see Example 6 and "Guanosine-30" data in FIG. 8). Injection of guanosine after 30 minutes of MCAO (just prior to removal of sutures) produced a dose-dependent decrease in infarct volume (see Example 6 and "Guanosine+30" data in FIG. 8). No neuroprotection was seen using the guanosine metabolite, inosine (INN in FIG. 8). The neuroprotective effect of guanosine appeared to be most prominent when injected immediately before suture removal (see +30 data point in FIG. 9 and Example 6) but significant neuroprotection was still observed when guanosine was injected 30 minutes after the onset of reperfusion (see +60 data point in FIG. 9).

Thus, it has been shown that the aforementioned animal model produces a highly reproducible focal infarct substantially restricted to the cerebral cortex, and that rodent mortality rate during the ischemia-reperfusion period is extremely low. The results with three known neuroprotectants, estrogen, edaravone and guanosine, demonstrate that a valid model to study human stroke and reperfusion injury has been provided. The results also demonstrate the potential use of the model to study the neuroprotective benefits of various therapeutics on the effects of stroke and reperfusion injury.

In some embodiments, the animal model may be used to examine the process and/or effects of ischemia and/or reperfusion. Good models of reperfusion injury are lacking in the prior art. A basic understanding of the mechanisms and pathways which are involved in ischemia and reperfusion injury may assist in the development of therapeutics and interventions which can minimize the detrimental effects associated therewith. Furthermore, treatments can be examined with respect to time of treatment versus onset of ischemia and/or reperfusion.

In some embodiments, the model permits the effects of reperfusion injury to be distinguished from the effects of ischemic injury.

In some embodiments, the model permits the effects of putative therapeutics on reperfusion injury to be distinguished from the effects on ischemic injury.

Further, in another aspect, there is provided a use of the aforementioned animal model for the study of stroke.

In another aspect, there is provided a method of screening or identifying compounds effective for treating stroke or testing compounds for effectiveness in treating stroke.

In certain embodiments, method of screening, identifying or testing compounds may be for screening, identifying or testing compounds for effectiveness in treating, reducing or preventing reperfusion injury.

In some embodiments, a test animal may be treated with a candidate compound or other intervention strategy, subjected to MCAO, or MCAO followed by reperfusion, and evaluated for extent of injury, which may include brain damage. The animal so treated could be compared to an appropriate control animal, for example, treated with a control compound or intervention, or receiving placebo or sham treatment, and subjected to the same MCAO or MCAO/reperfusion procedures. Decrease in injury, which may include brain damage (for example, decreased infarct volume), in the test animal is indicative of a compound or intervention useful in the treatment, reduction or prevention of ischemia and/or reperfusion injury, and potentially for treating stroke in a human. The timing of the intervention can be manipulated in order to identify compounds and interventions that may be useful in treating ischemic events associated with stroke or treating or preventing subsequent reperfusion injury.

In other embodiments, the effect of a candidate drug or compound on reperfusion injury may be specifically evaluated. This could be done, for example, by administering the drug after the MCAO, but immediately prior to removal of the sutures (reperfusion). In this way, the infarct core has already developed and the growth of the infarct in strictly due to reperfusion injury. Any change in size of infarct may be due to protection against reperfusion injury alone.

In some embodiments of the methods disclosed herein, a significant decrease in injury may measured as a decrease in infarct volume of greater than about 10%, 15%, 20%, 25%, 30%, 35%, 40%, 45%, 50%, 55%, 60%, 65%, 70%, 75%, 80%, 85%, 90%, 95%, 98%, 99% or 100%. About typically refers to a variance of +/−5%.

The most common method for quantifying the size (area or volume) of the lesion is using histological stains for cell viability and then using a scanner to digitize the images, followed by morphological assessment of infarct volume or area using computer assisted software (NIH image or Image J are free and most popular). Multiple stains for cell viability are available, however, the most popular and "trusted" gold standard method is using 2,3,5-triphenyltetrazolium chloride (TTC) which stains the tissue "pink" if they are alive and dead cell do not take up the stain and remain "white". This technique has been used, regardless of stroke model, since 1986 (see, for example, Regan et al., J Pharm Tox Met, 2007, 56: 339-343; Bederson et al., Stroke, 1986, 17(6): 1304-1308) and more recently has been shown to be as accurate as MRI (Goldlust et al., Stroke, 1996; 27:1657-1662) could not get pdf of article, so hyperlink attached below).

In the Examples below, data were analyzed using a statistical software package (SigmaStat™ and SigmaPlot™; Jandel Scientific, Tujunga, Calif.). All data are presented as a mean±standard error of the mean (±S.E.M). Differences were considered statistically significant (shown as "*" in FIGS. 6 to 9) if p 0.05 by an analysis of variance (ANOVA) followed by a Bonferoni post-hoc analysis, or when only two groups were being compared, with the use of a Student's t-test.

EXAMPLE 1

Suture-induced Middle Cerebral Artery Occlusion (MCAO)

Methods: All experiments were carried out in accordance with the guidelines of the Canadian Council on Animal Care and were approved by the University of Prince Edward Island Animal Care Committee. All experiments were conducted on male Sprague-Dawley rats (n=4 to 6 animals per group); 200-300 g; Charles Rivers; Montreal, PQ, CAN). For all animals, food and tap water were available ad libitum.

Rats were anaesthetized with sodium thiobutabarbital (Inactin; RBI, Natick, Mass., USA; 100 mg/kg; ip). A polyethylene catheter (PE-10; Clay Adams, Parsippany, N.J., USA) was inserted into the right femoral vein to permit intravenous administration of drugs. An endotracheal tube was inserted to facilitate breathing. Body temperature was monitored by a digital rectal thermometer and maintained at 37±1° C.

Animals were placed in a David Kopf stereotaxic frame (Tujunga, Calif., USA) and the right MCA approached through a rostra-caudal incision of the skin and frontalis muscle at the approximate level of bregma. The frontalis and temporalis muscles were then reflected anteriorly and posteriorly to expose the squamosal bone to the point where the zygoma and the squamosal bone fuse. A portion of the squamosal bone was then removed to expose the middle cerebral artery. The bent tip of a 25-gauge hypodermic needle was used to cut and retract the dura mater above the MCA. Blood flow through the MCA was impeded by the placement of surgical suture behind the MCA at 3 designated positions along the exposed vessel. The first suture (000-braided silk, Ethicon, N.J., USA) placement was made just dorsal to the rhinal fissure. A 20 cm length of suture was used. Half the length of the suture was threaded behind the MCA. The two ends were then gently pulled together and taped to the ear bars so that the resulting pressure on the MCA was sufficient to impede blood flow. The second suture (3-0 PROLINE™ brand blue monofilament, 2 cm in length, Ethicon, N.J., USA) was threaded behind the MCA just ventral to the bifurcation of the MCA to the frontal and parietal cortices, and the third suture (4-0 PROLINE™ brand blue monofilament, 2 cm in length, Ethicon, N.J., USA) was threaded behind the MCA just proximal to the bifurcation of the MCA along the parietal cortex. The ends of the second and third sutures were placed so that the middle of the sutures applied pressure to the MCA from behind and impeded blood flow through the MCA. Placement of the sutures, in accordance with one embodiment of the invention, is depicted in FIG. 1. This 3-point placement of surgical sutures produced a highly reproducible and consistent focal ischemic lesion volumes restricted to the ipsilateral cerebral cortex.

Suture placements were removed to induce reperfusion.

Results: Using this method, direct visualization of suture placement is permitted. Additionally, visualization and confirmation of occlusion and reperfusion (both the occurrence and the extent thereof) is facilitated. FIG. 1 depicts photomicrographs illustrating a right sided view of the rat brain and the MCA. The exposed rat brain is shown prior to suture placement in the top panel illustrating the MCA ("MCA" in FIG. 1A). The middle panel illustrates the placement of the 3 sutures ("Time 0" in FIG. 1B). The bottom panel illustrates the return of blood flow into the MCA 10 minutes following suture removal ("10 min post" in FIG. 10).

Figure 2:
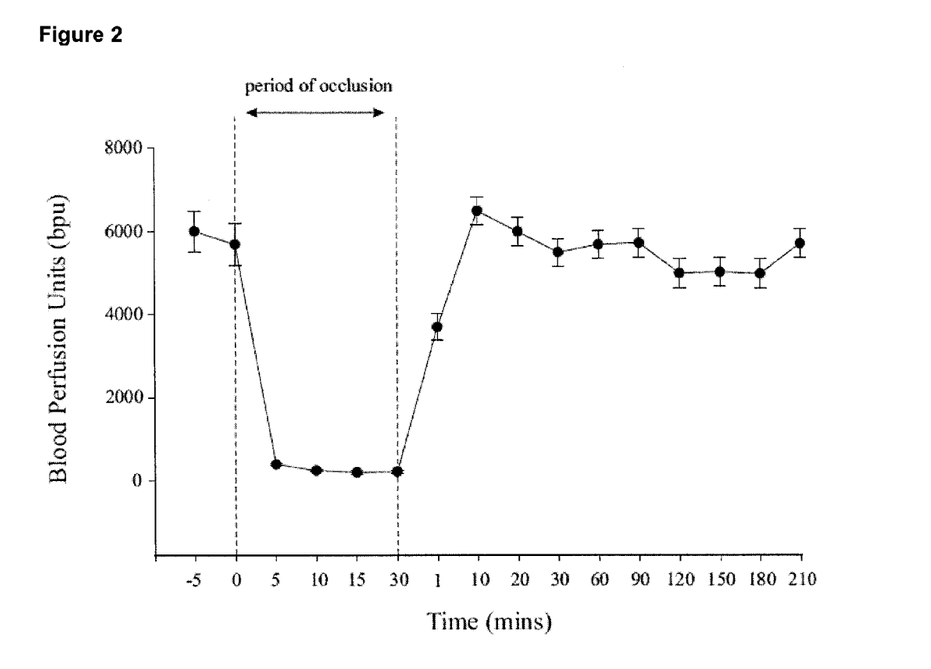
FIG. 2 is a graph depicting blood flow through the middle cerebral artery (MCA) in blood perfusion units (bpu) prior to, during and post suture removal.

FIG. 2 depicts a graph of cerebral blood flow which confirms the occlusion and reperfusion. Blood flow through the MCA is depicted in blood perfusion units (bpu) prior to (−5 to 0 minutes), during (0 to 30 minutes) and post suture removal (30 to 210 minutes). Dashed lines represent the 30-minute period during which the sutures were on the MCA. Data points represent the mean±S.E.M.

This approach resulted in a highly reproducible focal ischemic injury restricted to the prefrontal cerebral cortex with an intraoperative mortality rate of less than 2%. As an example, FIG. 3 depicts serial sections of a rat brain (following 30 minutes of occlusion followed by 5.5 hours of reperfusion) are shown as photomicrographs of TTC-stained, 1 mm thick coronal sections illustrating the extent of the infarct (white areas) within the prefrontal cortex.

EXAMPLE 2

Effect of Occlusion Time on Infarct Volume

The following experiment was designed to determine if a time-dependent relationship existed between MCAO and infarct volume.

Method: MCAO was carried out as described in Example 1. The three sutures were left in place for 0.5, 2, 4, or 6 hours. Following the removal of the sutures, all animals were perfused transcardially with phosphate buffered saline (PBS; 0.1 M; 200 mls), the brains removed and sliced into 1 mm coronal sections using a rat brain matrix (Harvard Apparatus; Holliston, Mass., USA). Sections were incubated in a 2% solution of 2,3,5-triphenol tetrazolium chloride (TTC; Sigma-Aldrich; St. Louis; Mo., USA) for 5 minutes.

Infarct volumes were calculated with the use of scanned digital images of each brain section. The infarct area for both sides of each brain section was calculated using a computer-assisted imaging system (Scion Corporation; Frederick, Md., USA). The infarct areas for each side for each individual section were averaged and multiplied by the width of each section (1 mm) to give the infarct volume for each section. The sum total of all the individual infarct volumes provided the infarct volume for each rat.

Results: A time-dependent relationship existed on infarct volume following suture-induced MCAO (see FIG. 4). The three sutures were left in place for 0.5, 2, 4, or 6 hours. The infarct volume following 0.5 hours of suture placement (n=4) was minimal ($0.7 \pm 0.06$ mm$^3$). The infarct volume following 2 hours of suture placement ($14.6 \pm 2.4$ mm$^3$; n=6) was significantly greater than the 0.5 hour placement ($p<0.05$). The infarct volumes for the 4 ($27.7 \pm 2.6$ mm$^3$; n=6) and 6 ($28.1 \pm 1.6$ mm$^3$; n=6) hour placements were not significantly different from each other ($p>0.05$) and each was significantly greater that the 2 hour infarct size ($p<0.05$) for each comparison.

This approach resulted in a significantly larger infarct volume compared to occlusion alone (reperfusion injury). This approach also resulted in a highly reproducible focal ischemic injury restricted to the prefrontal cerebral cortex with an intraoperative mortality rate of less than 2%. Further, this model allowed visual verification that blood flow has been impeded with the placement of sutures behind the middle cerebral artery that blood flow returns once the sutures are removed.

EXAMPLE 3

Effect of Reperfusion on Infarct Volumes

The following experiment was designed to investigate the effect of reperfusion on infarct volume following MCAO.

Method: MCAO was carried out as described in Example 1. The sutures were left in place, thus impeding blood flow through the MCA, for 0.5, 2 and 4 hrs. For the 0.5 hour group (n=9), blood flow was returned for 5.5 hours; for the 2 hour group (n=6), blood flow was returned for 4 hours; and for the 4 hour group (n=6), blood flow was returned for 2 hours. In an additional validation group (n=6), the sutures were put in place and immediately removed, and blood flow was allowed to return for 6 hours. In all cases, the return of blood flood was visually confirmed with the use of a dissecting microscope. In all groups, the experiment was terminated at the 6 hour time point.

At the end of six hours all animals were treated and infarct volumes determined as set out in Example 2.

Results: There was a progressive increase in infarct volume as the length of time on the initial infarct was increased (see FIG. 5) from the immediate removal of the sutures (data point 0.1/6 in FIG. 5) to when the sutures were left in place for the full 6 hours (data point 6/0 in FIG. 5). Immediate removal of the sutures resulted in an infarct volume of $4.5 \pm 0.7$ mm$^3$ (n=4). Leaving the sutures in for 30 minutes and allowing the return of blood flow for 5.5 hours (data point 0.5/5.5) resulted in an infarct volume of $11.7 \pm 2.1$ mm$^3$ (n=9). Leaving the sutures in for 2 hours and allowing the return of blood flow for 4 hours (data point 2/4) resulted in an infarct volume of $17.0 \pm 1.7$ mm$^3$ (n=6). Leaving the sutures in place for 4 hours and allowing the return of blood flow for 2 hours (data point 4/2) resulted in an infarct volume of $34.2 \pm 5.0$ mm$^3$ (n=6). The infarct volume when the sutures were left in place for the full 6 hours was $28.1 \pm 1.6$ mm$^3$; n=6; data point 6/0. The most significant increase in infarct volume due to reperfusion was found when the sutures were left in place for 30 minutes (data point 0.5 in FIG. 4; $0.76 \pm 0.06$ mm$^3$), compared to when the sutures were removed after the 30 minute time point, and when blood flow was allowed to return for 5½hours (data point 0.1/6 in FIG. 5; $11.7 \pm 2.1$ mm$^3$; $p<0.05$).

EXAMPLES 4

Effect of Estrogen or Edaravone on Infarct Volume

Estrogen has been demonstrated to be a powerful neuroprotectant when administered prior to MCA occlusion using electrical bipolar coagulation (Saleh et al., 2001a, 2001b). The following experiment was designed to investigate the effect of estrogen or edaravone on infarct volume following "permanent" (6-hour) MCAO.

Method: We sought to determine if estrogen would be as effective a neuroprotectant when blood flow through the MCA was impeded with sutures. Estrogen ($1 \times 10$-2 mg/kg; 0.2 mls; i.v.; Sigma-Aldrich) or saline (0.2 ml; i.v.) was administered 30 minutes prior to the placement of sutures according to the MCAO method of Example 1. The sutures remained in place for 6 hours. Edaravone, shown to have powerful anti-ischemic and anti-reperfusion-injury properties was used to determine if it would be effective in this suture model. Edaravone at doses of 1, 5, 10, 20 and 40 mg/kg (0.2 ml; i.v.; Sigma-Aldrich) was administered 30 minutes prior to the placement of the sutures. In addition, a group injected with 50% DMSO in saline (edaravone vehicle; 0.2 ml) was administered 30 minutes prior to the placement of the sutures.

At the end of six hours all animals were treated and infarct volumes determined as set out in Example 2.

Results: Referring to FIG. 6, the administration of estrogen 30 minutes prior to 6 hours of suture induced-MCAO (E2-30 data point) resulted in a significant decrease in infarct size compared to the administration of estrogen vehicle (sal-30 data point; $p<0.05$). Administration of edaravone (see Edaravone-30' data in FIG. 6; numerals are indicative of mg/kg dose of edaravone) at 10, 20 or 40 mg/kg at 30 minutes prior to 6 hours of suture induced-MCAO resulted in significant decreases in infarct size compared to the infarct volume following the administration of edaravone vehicle, 50% DMSO in saline (dmso-30 data point; $p<0.05$ for each comparison).

EXAMPLE 5

The Effect of Estrogen or Edaravone on Reperfusion Injury

The following experiment was designed to investigate the effect of estrogen or edaravone on infarct volume following MCAO.

Method: We sought to determine if estrogen would be as effective a neuroprotectant for reperfusion injury as it was for straight ischemic injury. Estrogen ($1 \times 10$-2 mg/kg; 0.2 ml; i.v.; Sigma-Aldrich) or saline (0.2 mls; i.v.) was administered 30 minutes following the placement of the sutures in accordance with the MCAO method of Example 1 (i.e. immediately prior to the removal of the sutures) and blood flow was allowed to return to the MCA for 5 ½ hours. Edaravone at doses of 1, 5, 10 and 20 mg/kg (0.2 ml; i.v.; Sigma-Aldrich) or 50% DMSO in saline (edaravone vehicle; 0.2 ml) was administered 30 minutes following the placement of the sutures (immediately prior to the removal of the sutures) and blood flow was allowed to return for 5 ½ hours. In addition, a group injected with 50% DMSO in saline (edaravone vehicle; 0.2 ml) was administered 30 minutes after the placement of the sutures.

At the end of six hours all animals were treated and infarct volumes determined as set out in Example 2.

Results: Referring to FIG. 7, the administration of estrogen 30 minutes after suture induced-MCAO followed by 5.5 hours of reperfusion (E2+30 data point) resulted in a significant decrease in infarct size compared to the administration of estrogen vehicle at the same time (sal+30 data; p<0.05). Administration of edaravone at 5, 10 or 20 mg/kg 30 minutes after 30 minutes of MCAO followed by 5.5 hours of reperfusion (see Edaravone+30' data in FIG. 7; numerals are indicative of the mg/kg dose) resulted in significant decreases in infarct size compared to the infarct volume following the administration of edaravone vehicle, 50% DMSO in saline (dmso+30 data point; p<0.05 for each comparison).

EXAMPLE 6

The Effect of Guanosine on Reperfusion Injury

The following experiments were designed to investigate the effects of guanosine injected pre- or post-occlusion on infarct volume following MCAO.

Method: (i) MCAO was induced according to the method of Example 1. Guanosine was injected intraperitoneally at doses of 1, 2, 4, 8 or 16 mg/kg (a) 30 minutes prior to "permanent" (6-hour) occlusion or (b) immediately after 30 mins of occlusion prior to removal of sutures followed by 5.5 hours of reperfusion. A secondary metabolite of guanosine, inosine, was also tested at 16 mg/kg using the latter conditions. For both treatments, an additional group was administered guanosine vehicle (saline with 0.1N NaOH).

(ii) In a second experiment, guanosine was injected at a dose of 16 mg/kg at 30, 60 and 90 minutes after MCAO. In these experiments, sutures were always removed 30 minutes after initiation of the MCAO. A control group for each time was injected with corresponding guanosine vehicle.

Results: (i) Referring to FIG. 8, injection of guanosine 30 minutes prior to "permanent" (6-hour) ischemia (see 'Guanosine-30' data) resulted in decrease in infarct volume. A dose-dependent decrease was observed when guanosine was injected 30 minutes after MCAO followed by 5.5h reperfusion (see 'Guanosine+30' data). Numerals at each of the various guanosine data points in FIG. 8 are indicative of dosage in mg/kg. No such effect was observed for guanosine vehicle (16V). Inosine (INN) also did not cause neuroprotection, suggesting that the neuroprotection is specific to guanosine.

Figure 9:
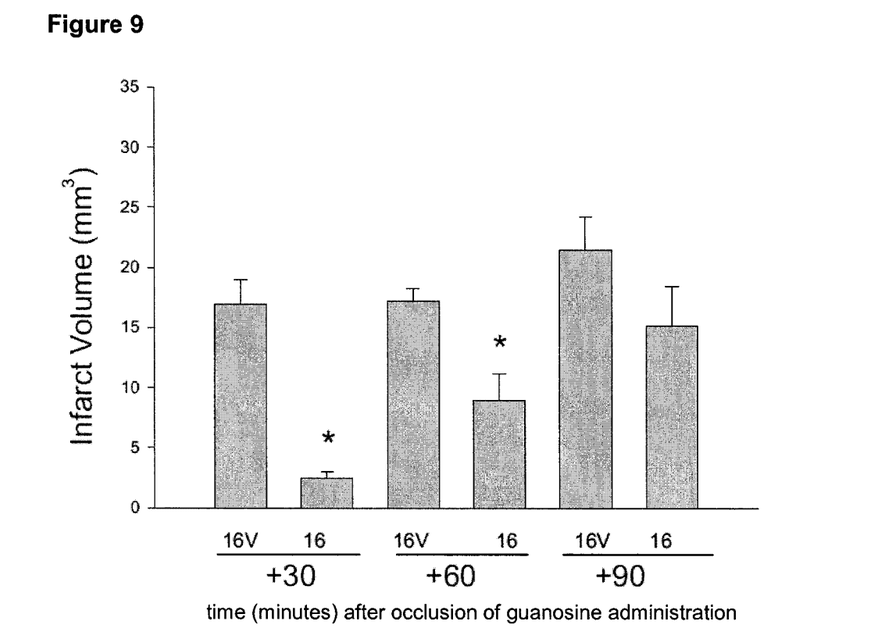
FIG. 9 is a graph depicting the effect of guanosine injected post-occlusion on infarct volume due ischemia and/or ischemia/reperfusion induced using methods according to certain embodiments of the invention.

(ii) FIG. 9 shows the neuroprotective effect of guanosine at a dose of 16 mg/kg (see '16' data points) injected 30 minutes (+30) after occlusion (i.e. immediately prior to removal of sutures) as well as at 60 minutes (+60) and 90 minutes (+90) post-occlusion, as compared to corresponding guanosine vehicle alone (see 16V data points). The greatest benefit was observed when the drug was administered immediately prior to suture removal (+30). Of importance, a significant benefit was still observed when the drug was administered 30 minutes post-suture removal (i.e. the +60 data point; 60 minutes from start of MCAO).

All references cited herein are expressly incorporated by reference.

In the preceding description, for purposes of explanation, numerous details are set forth in order to provide a thorough understanding of the embodiments of the invention. However, it will be apparent to one skilled in the art that these specific details are not required in order to practice the invention. The above-described embodiments of the invention are intended to be examples only. Alterations, modifications and variations can be effected to the particular embodiments by those of skill in the art without departing from the scope of the invention, which is defined solely by the claims appended hereto.

The invention claimed is:

1. A method of inducing reproducible brain ischemia and optionally reperfusion injury in a non-human mammal, the method comprising:
   exposing a portion of the middle cerebral artery (MCA) located in the area of the rhinal fissure and bifurcation of the MCA to the frontal and parietal cortices in the non-human mammal,
   temporarily occluding said MCA at a first location, a second location, and a third location to substantially occlude blood flow, wherein:
      the first location is proximally dorsal to the rhinal fissure;
      the second location is proximally ventral to bifurcation of said MCA to the frontal and parietal cortices; and
      the third location is proximal to bifurcation of said MCA along the parietal cortex;
   maintaining said occlusion for a time sufficient to induce a focal ischemia in the area of the MCA in the non-human mammal; and,
   optionally, releasing said occlusion to restore blood flow and maintaining said restored blood flow for a time sufficient to induce a reperfusion injury.

2. The method of claim 1, wherein a suture material is used to temporarily occlude said MCA at said first, second and third locations.

3. The method of claim 2, wherein to provide the temporary occlusion
   a first suture is threaded behind said MCA at said first location,
   a second suture is threaded behind said MCA at said second location, and
   a third suture is threaded behind said MCA at said third location.

4. The method of claim 3, wherein a force is applied to the first suture in a direction substantially perpendicular to the axis of the MCA at the first location to occlude said MCA at said first location, and wherein placement of the second and third sutures behind the MCA at the second and third locations is sufficient for occlusion at said second and third locations.

5. The method of claim 3, wherein
   said first suture comprises 000-braid silk,
   said second suture comprises a monofilament size 3-0 suture, and
   said third suture comprises a monofilament size 4-0 suture.

6. The method of claim 1, wherein the occlusion time is about 0.3 to about 10 hours.

7. The method of claim 6, wherein the occlusion time is about 0.5 to about 6 hours.

8. The method of claim 7, wherein the occlusion time is about 0.5 to about 1 hour.

9. The method of claim 1, wherein the reperfusion time is about 0.3 to about 10 hours.

10. The method of claim 9, wherein the reperfusion time is about 3 to about 10 hours.

11. The method of claim 10, wherein the reperfusion time is about 4 to about 6 hours.

12. The method of claim 1, wherein the occlusion time is about 0.3 hours to about 1 hour and the reperfusion time is about 4 to about 6 hours.

13. The method of claim 12, wherein the occlusion time is about 0.5 hours and the reperfusion time is about 5.5 hours.

14. A method of identifying a compound or intervention useful in the treatment, reduction or prevention of a focal brain ischemia in the region of the middle cerebral artery (MCA) and optionally reperfusion injury the method comprising:
- subjecting a test animal which is a non-human mammal to the method of claim 1;
- administering a test compound or intervention to the test animal prior to, during, or after administering the method, or a combination thereof; and
- assessing the extent of focal injury compared to an appropriate control animal, wherein a decrease in the extent of focal ischemia in the test animal compared to the control animal is indicative that the compound or intervention is useful in the treatment, reduction, or prevention of focal brain ischemia in the region of the MCA, and optionally reperfusion injury.

15. The method of claim 1, wherein the non-human mammal is a rodent.

16. The method of claim 15, wherein the rodent is a rat.

17. A method of inducing reproducible brain ischemia and optionally reperfusion injury in a rat, the method comprising:
- exposing a portion of the middle cerebral artery (MCA) located in the area of the rhinal fissure and bifurcation of the MCA to the frontal and parietal cortices in the rat;
- temporarily occluding said MCA at a first location, a second location, and a third location to substantially occlude blood flow, wherein the first location is proximally dorsal to the rhinal fissure, the second location is proximally ventral to bifurcation of said MCA to the frontal and parietal cortices, and, the third location is proximal to bifurcation of said MCA along the parietal cortex;
- maintaining said occlusion for an occlusion time of about 0.3 hours to about 1 hour;
- optionally releasing said occlusion to restore blood flow and maintaining said restored blood flow for a reperfusion time of about 4 to about 6 hours; and
- assessing the type and extent of focal ischemia produced.

18. A method of identifying a compound or intervention useful in the treatment, reduction, or prevention of a focal brain ischemia in the region of the middle cerebral artery (MCA) and optionally reperfusion injury the method comprising:
- exposing a portion of the MCA in a test animal which is a rat;
- temporarily occluding said MCA at a first location, a second location, and a third location to substantially occlude blood flow, wherein the first location is proximally dorsal to the rhinal fissure, the second location is proximally ventral to bifurcation of said MCA to the frontal and parietal cortices, and, the third location is proximal to bifurcation of said MCA along the parietal cortex;
- maintaining said occlusion for an occlusion time of about 0.3 hours to about 1 hour;
- optionally releasing said occlusion to restore blood flow and maintaining said restored blood flow for a reperfusion time of about 4 to about 6 hours;
- administering a test compound or intervention to the test animal prior to, during, or after the occlusion period, the reperfusion period, or both, or a combination thereof; and
- assessing the extent of focal ischemia compared to an appropriate control animal, wherein a decrease in the extent of focal ischemia in the test animal compared to the control animal is indicative that the compound or intervention is useful in the treatment, reduction, or prevention of focal brain ischemia in the region of the MCA, and optionally reperfusion injury.

19. The method of claim 17, wherein the occlusion time is about 0.5 hours and the reperfusion time is about 5.5 hours.

20. An animal model of ischemic stroke, and optionally reperfusion injury, comprising a nonhuman mammal in which a focal brain ischemia is induced in the region of the middle cerebral artery (MCA) by subjecting said nonhuman mammal to the method of claim 1.

* * * * *